(12) United States Patent (10) Patent No.: US 10,202,362 B2
Roinestad et al. (45) Date of Patent: Feb. 12, 2019

(54) INHIBITORS OF LEUKOTRIENE A4 HYDROLASE

(71) Applicant: Celtaxsys, Inc., Atlanta, GA (US)

(72) Inventors: Kurt Roinestad, Atlanta, GA (US); William Guilford, Belmont, CA (US); Tom Kirkland, Atascadero, CA (US); Lopa Bhatt, Roswell, GA (US); Eric Springman, Atlanta, GA (US)

(73) Assignee: Celtaxsys, Inc., Atlanta, GA (US)

( * ) Notice: Subject to any disclaimer, the term of this patent is extended or adjusted under 35 U.S.C. 154(b) by 0 days.

(21) Appl. No.: 15/837,515

(22) Filed: Dec. 11, 2017

(65) Prior Publication Data

US 2018/0162836 A1 Jun. 14, 2018

Related U.S. Application Data

(60) Provisional application No. 62/432,231, filed on Dec. 9, 2016.

(51) Int. Cl.
| | |
|---|---|
| *C07D 401/06* | (2006.01) |
| *A61P 29/00* | (2006.01) |
| *C07D 413/12* | (2006.01) |
| *C07D 211/34* | (2006.01) |
| *C07D 413/14* | (2006.01) |
| *C07D 211/32* | (2006.01) |

(52) U.S. Cl.
CPC ............ *C07D 401/06* (2013.01); *A61P 29/00* (2018.01); *C07D 211/32* (2013.01); *C07D 211/34* (2013.01); *C07D 413/12* (2013.01); *C07D 413/14* (2013.01)

(58) Field of Classification Search
CPC .................................................... C07D 401/06
USPC ........................................................ 546/187
See application file for complete search history.

(56) References Cited

U.S. PATENT DOCUMENTS

| 7,737,145 B2 | 6/2010 | Arnaiz et al. |
| 2010/0210630 A1 | 8/2010 | Arnaiz et al. |

OTHER PUBLICATIONS

International Search Report and Written Opinion dated Mar. 13, 2018 in corresponding International Application No. PCT/US2017/065571.
Khim et al, "Discovery of novel and potent aryl diamines as leukotriene A4 hydrolase inhibitors", Bioorganic & Medicinal Chemistry Letters, vol. 18, No. 14, Jul. 15, 2008, pp. 3895-3898.

*Primary Examiner* — Taofiq A Solola
(74) *Attorney, Agent, or Firm* — Elmore Patent Law Group, P.C.; Mahreen Chaudhry Hoda; Carolyn S. Elmore

(57) ABSTRACT

This present disclosure is directed to compounds of formula (I):

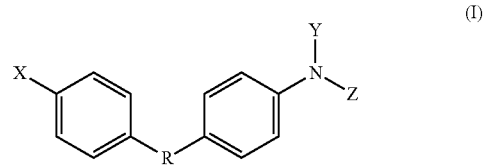

where $R^{1a}$, $R^3$, Y, and Z are described herein, as single stereoisomers or as mixtures of stereoisomers, or pharmaceutically acceptable salts, solvates, clathrates, polymorphs, ammonium ions, N-oxides or prodrugs thereof; which are leukotriene $A_4$ hydrolase inhibitors and therefore useful in treating inflammatory disorders. Pharmaceutical compositions including the compounds described herein and methods of preparing the compounds described herein are also provided.

13 Claims, No Drawings

INHIBITORS OF LEUKOTRIENE A4 HYDROLASE

CROSS-REFERENCE TO RELATED APPLICATION

The instant patent application claims the benefit of and priority to U.S. Provisional Patent Application Ser. No. 62/432,231 filed on Dec. 9, 2016, the entire content of which is incorporated herein by reference.

TECHNICAL FIELD

This present disclosure describes compounds which include substituted amines and derivatives suitable as leukotriene A4 hydrolase inhibitors and useful in treating inflammatory disorders.

BACKGROUND

Leukotriene $B_4$ ($LTB_4$) is a potent pro-inflammatory activator of inflammatory cells, including neutrophils, monocytes, macrophages, T cells and B cells. Immune cell priming and activation by $LTB_4$ can promote chemotaxis, adhesion, free radical release, degranulation and cytokine release. $LTB_4$ plays a significant role in the amplification of many inflammatory disease states including asthma, inflammatory bowel disease (IBD), chronic obstructive pulmonary disease (COPD), arthritis, psoriasis, and atherosclerosis.

$LTB_4$ levels are elevated in brochoalveolar lavage fluid from patients with scleroderma lung disease. Therefore, a therapeutic agent that inhibits the biosynthesis of LTB4 or the response of cells to $LTB_4$ may be useful for the treatment of these inflammatory conditions.

The biosynthesis of $LTB_4$ from arachidonic acid (AA) involves the action of three enzymes: phospholipase $A_2$ ($PLA_2$), to release AA from the membrane lipids; 5-lipoxygenase (5-LO), to form the unstable epoxide Leukotriene $A_4$ ($LTA_4$); and leukotriene $A_4$ hydrolase ($LTA_4$-h), to form $LTB_4$.

$LTA_4$-h is a monomeric, soluble 69 kD bifunctional zinc-dependent metalloenzyme of the M1 class of metallohydrolases. It catalyzes two reactions: the stereospecific epoxide hydrolase reaction to convert $LTA_4$ to $LTB_4$ and a peptidase cleavage of chromogenic substrates. A reduction of $LTB_4$ production by an inhibitor of $LTA_4$-h activity has therapeutic potential in a wide range of diseases. $LTA_4$-h inhibitors have been shown to be effective anti-inflammatory agents in preclinical studies, thus providing the ability to prevent and/or treat leukotriene-mediated conditions, such as inflammation. $LTA_4$-h inhibitors are disclosed, for example, in U.S. Pat. No. 7,737,145 and U.S. Patent Application Publication No. 2010/0210630A1, the contents of each of which are incorporated by reference herein.

It would be advantageous to develop additional $LTA_4$-h inhibitors.

SUMMARY

Compounds in accordance with the present disclosure inhibit the activity of $LTA_4$-h and are therefore useful as pharmaceutical agents for the treatment of diseases and disorders which are ameliorated by the inhibition of $LTA_4$-h activity.

In one aspect, the disclosure provides compounds of Formula (I), as single stereoisomers or as mixtures of stereoisomers, or pharmaceutically acceptable salts, solvates, polymorphs, clathrates, ammonium ions, N-oxides or prodrugs thereof, that:

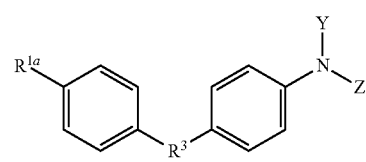

(I)

wherein $R^{1a}$ is hydrogen, halo, haloalkyl, haloalkenyl, haloalkynyl, hydroxyalkyl, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, optionally substituted amidinyl, optionally substituted guanidinyl, —$R^{13}$—$OR^{10}$, —$R^{13}$—C(=O)$OR^{10}$), or —$R^{13}$—C(=O)$R^{10}$;

$R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain, —$R^{13}$—C(=O)$R^{13}$, —O—$R^{13}$—C(=O)$R^{13}$, —$R^{13}$—O—$R^{13}$—C(OH)—$R^{13}$, or —$NR^{13}$—;

Y is hydrogen, halo, haloalkyl, haloalkenyl, haloalkynyl, hydroxyalkyl, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, or optionally substituted heterocyclylalkyl;

Z is

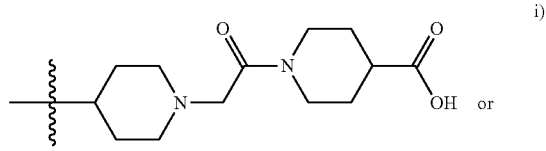

i)

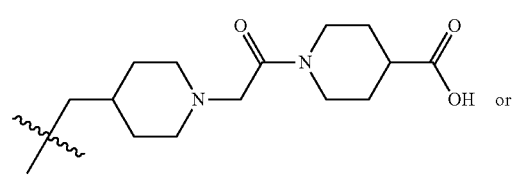

ii)

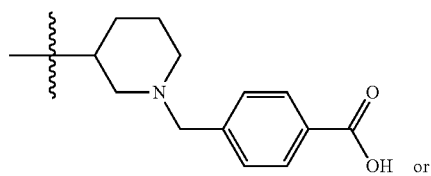

iii)

or

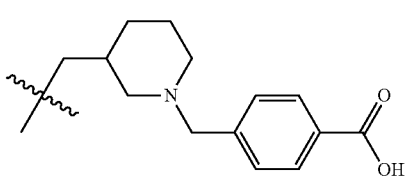

(iv)

each $R^{10}$ is independently hydrogen, haloalkyl, haloalkenyl, haloalkynyl, hydroxyalkyl, optionally substituted alkyl, optionally substituted alkenyl, optionally substituted alkynyl, optionally substituted aryl, optionally substituted aralkyl, optionally substituted heteroaryl, optionally substituted heteroarylalkyl, optionally substituted heterocyclyl, or optionally substituted heterocyclylalkyl;

each $R^{12}$ is independently an optionally substituted straight or branched alkylene chain, an optionally substituted straight or branched alkenylene chain, or an optionally substituted straight or branched alkynylene chain;

each $R^{13}$ is independently a direct bond, an optionally substituted straight or branched alkylene chain, an optionally substituted straight or branched alkenylene chain, or an optionally substituted straight or branched alkynylene chain;

as a single stereoisomer or as a mixture of stereoisomers;

or a pharmaceutically acceptable salt, solvate, polymorph, clathrate, ammonium ion, N-oxide or prodrug thereof.

In another aspect, the present disclosure provides pharmaceutical compositions, which composition comprises a therapeutically effective amount of a compound of formula (I) as described above, and a pharmaceutically acceptable excipient.

In another aspect, the present disclosure provides a method of treating a disease or disorder ameliorated by the inhibition of $LTA_4$-h activity in a mammal, which method comprises administering to a mammal in need thereof a therapeutically effective amount of a compound of formula (I) as described above.

DETAILED DESCRIPTION

A detailed description of exemplary embodiments are described in the disclosure that follows.

As used herein, the word "a" and "an" are meant to include one or more unless otherwise specified. For example, "a compound" refers to one or more of such compounds.

Furthermore, as used in the specification and appended claims, unless specified to the contrary, the following terms have the meaning indicated:

"Amino" refers to the —$NH_2$ radical.
"Cyano" refers to the —CN radical.
"Hydroxy" refers to the —OH radical.
"Nitro" refers to the —$NO_2$ radical.
"Oxo" refers to the =O radical.
"Alkyl" refers to a straight or branched hydrocarbon chain radical consisting solely of carbon and hydrogen atoms, containing no unsaturation and which is attached to the rest of the molecule by a single bond. In some embodiments, an alkyl group has from one to twelve carbon atoms, one to eight carbon atoms, or one to six carbon atoms. Non-limiting examples of alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like. An optionally substituted alkyl group can be an alkyl group substituted with one or more substituents described in detail below. Non-limiting examples of suitable substituents include: halo, cyano, nitro, oxo, trimethylsilyl, —$OR^{15}$—, —OC(=O)—$R^{15}$, —N($R^{15}$)$_2$, —C(=O)—$R^{15}$, —C(=O)O$R^{15}$, —C(=O)N($R^{15}$)$_2$, —N($R^{15}$)C(=O)O$R^{15}$, —N($R^{15}$)C(=O)—$R^{15}$, —N($R^{15}$)S(=O)$_t R^{15}$ (where t is 1 or 2), —S(=O)$_t OR^{15}$ (where t is 1 or 2), —S(=O)$_p R^{15}$ (where p is 0, 1 or 2), and —S(=O)$_t N(R^{15})_2$ (where t is 1 or 2) where each $R^{15}$ is independently hydrogen, alkyl, haloalkyl, cycloalkyl, cycloalkylalkyl, aryl (optionally substituted with one or more halo or alkyl groups), aralkyl, heterocyclyl, heterocyclylalkyl, heteroaryl or heteroarylalkyl, and where each of the above substituents is unsubstituted unless specifically defined otherwise.

"Alkenyl" refers to a straight or branched hydrocarbon chain radical group consisting solely of carbon and hydrogen atoms, containing at least one double bond, having from two to twelve carbon atoms, in embodiments two to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl group may be optionally substituted by one of the following substituents: cyano, nitro, oxo, trimethylsilyl, —$OR^{15}$, —OC(=O)—$R^{15}$, —N($R^{15}$)$_2$, —C(=O)—$R^{15}$, —C(=O)O$R^{15}$, —C(=O)N($R^{15}$)$_2$, —N($R^{15}$)C(=O)O$R^{15}$, —N($R^{15}$)C(=O)$R^{15}$, —N($R^{15}$)S(=O)$_t R^{15}$ (where t is 1 or 2), —S(=O)$_t OR^{15}$ (where t is 1 or 2), —S(=O)$_p R^{15}$ (where p is 0, 1 or 2), and —S(=O)$_t N(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless specifically defined otherwise.

"Alkynyl" refers to a straight or branched hydrocarbon chain radical group consisting solely of carbon and hydrogen atoms, containing at least one triple bond, optionally containing at least one double bond, having from two to twelve carbon atoms, in embodiments two to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one of the following substituents: cyano, nitro, oxo, trimethylsilyl, —$OR^{15}$, —OC(=O)—$R^{15}$, —N($R^{15}$)$_2$, —C(=O)$R^{15}$, —C(=O)O$R^{15}$, —C(=O)N($R^{15}$)$_2$, —N($R^{15}$)C(=O)O$R^{15}$, —N($R^{15}$)C(=O)$R^{15}$, —N($R^{15}$)S(=O)$_t R^{15}$ (where t is 1 or 2), —S(=O)$_t OR^{15}$ (where t is 1 or 2), —S(=O)$_p R^{15}$ (where p is 0, 1 or 2), and —S(=O)$_t N(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless specifically defined otherwise.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain.

Unless stated otherwise specifically in the specification, an alkylene chain may be optionally substituted by one of the following substituents: halo, cyano, nitro, aryl, cycloalkyl, heterocyclyl, heteroaryl, oxo, trimethylsilyl, —OR$^{15}$, —OC(=O)—R$^{15}$, —N(R$^{15}$)$_2$, —C(=O)R$^{15}$, —C(=O)OR$^{15}$, —C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless specifically defined otherwise.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following substituents: halo, cyano, nitro, aryl, cycloalkyl, heterocyclyl, heteroaryl, oxo, trimethylsilyl, —OR$^{15}$, —OC(=O)—R$^{15}$, —N(R$^{15}$)$_2$, —C(=O)R$^{15}$, —C(=O)OR$^{15}$, —C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following substituents: alkyl, alkenyl, halo, haloalkenyl, cyano, nitro, aryl, cycloalkyl, heterocyclyl, heteroaryl, oxo, trimethylsilyl, —OR$^{15}$, —OC(=O)—R$^{15}$, —N(R$^{15}$)$_2$, —C(=O)R$^{15}$, —C(=O)OR$^{15}$, —C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —R$_a$—O—R$_a$, where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Amidinyl" refers to a radical of the formula R$_x$—C(=NR$_x$)—N(R$_x$)$_2$ wherein each R$_x$ is independently a direct bond, hydrogen, an alkyl, alkenyl, alkynyl, aryl, aralkyl, cycloalkyl, cycloalkylalkyl, heterocyclyl, heteroaryl, heteroarylalkyl as defined herein.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{16}$—OR$^{15}$, —R$^{16}$—OC(=O)—R$^{15}$, —R$^{16}$—N(R$^{15}$)$_2$, —R$^{16}$—C(=O)R$^{15}$, —R$^{16}$—C(=O)OR$^{15}$, —R$^{16}$—C(=O)N(R$^{15}$)$^2$, —R$^{16}$—N(R$^{15}$)C(=O)OR$^{15}$, —R$^{16}$—N(R$^{15}$)C(=O)R$^{15}$, —R$^{16}$—N(R$^{15}$)C(=O)N(R$^{15}$)$^2$, —R$^{16}$—N(R$^{15}$)S(=O)$_t$R$^{15}$ (where t is 1 or 2), —R$^{16}$—S(=O)$_t$OR$^{15}$ (where t is 1 or 2), —R$^{16}$—S(=O)$_p$R$^{15}$ (where p is 0, 1 or 2), and —R$^{16}$—S(=O)$_t$N(R$^{15}$)$_2$ (where t is 1 or 2), where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each R$^{16}$ is independently a direct bond or a straight or branched alkylene or alkenylene chain.

"Aralkyl" refers to a radical of the formula —R$_a$R$_b$ where R$_a$ is an alkyl radical as defined above and R$_b$ is one or more aryl radicals as defined above, for example, benzyl, diphenylmethyl and the like. The aryl radical(s) may be optionally substituted as described above.

"Aralkenyl" refers to a radical of the formula —R$_c$R$_b$ where R$_c$ is an alkenyl radical as defined above and R$_b$ is one or more aryl radicals as defined above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula —R$_d$R$_b$ where R$_d$ is an alkynyl radical as defined above and R$_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Aryloxy" refers to a radical of the formula —OR$_b$ where R$_b$ is an aryl group as defined above. The aryl part of the aryloxy radical may be optionally substituted as defined above.

"Aralkyloxy" refers to a radical of the formula —OR$_b$ where R$_b$ is an aralkyl group as defined above. The aralkyl part of the aralkyloxy radical may be optionally substituted as defined above.

"Ammonium ion" refers to a nitrogen within a compound of the present disclosure containing a positive charge due to the additional substitution of the nitrogen with an optionally substituted alkyl group as defined above.

"Clathrates" as used herein refers to substances which fix gases, liquids or compounds as inclusion complexes so that the complex may be handled in solid form and the included constituent (or "guest" molecule) is subsequently released by the action of a solvent or by melting. The term "clathrate" is used interchangeably herein with the phrase "inclusion molecule" or with the phrase "inclusion complex". Clathrates used in the instant disclosure are prepared from cyclodextrins. Cyclodextrins are widely known as having the ability to form clathrates (i.e., inclusion compounds) with a variety of molecules. See, for example, *Inclusion Compounds*, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2-44; Weber, E. et al., "Functional Group Assisted Clathrate Formation—Scissor-Like and Roof-Shaped Host Molecules", *Topics in Current Chemistry* (1988), Vol. 149, pp. 45-135; and MacNicol, D. D. et al., "Clathrates and Molecular Inclusion Phenomena", *Chemical Society Reviews* (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344-362; U.S. Pat. No. 4,886,788 (Schering A G); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cyclodextrin" refers to cyclic oligosaccharides consisting of at least six glucopyranose units which are joined together by $\alpha(1-4)$ linkages. The oligosaccharide ring forms a torus with the primary hydroxyl groups of the glucose residues lying on the narrow end of the torus. The secondary glucopyranose hydroxyl groups are located on the wider end. Cyclodextrins have been shown to form inclusion complexes with hydrophobic molecules in aqueous solutions by binding the molecules into their cavities. The formation of such complexes protects the "guest" molecule from loss of evaporation, from attack by oxygen, visible and ultraviolet light and from intra- and intermolecular reactions. Such complexes also serve to "fix" a volatile material until the complex encounters a warm moist environment, at which point the complex will dissolve and dissociate into the guest molecule and the cyclodextrin. For purposes of this disclosure, the six-glucose unit containing cyclodextrin is specified as $\alpha$-cyclodextrin, while the cyclodextrins with seven and eight glucose residues are designated as $\beta$-cyclodextrin and $\gamma$-cyclodextrin, respectively. The most common alternative to the cyclodextrin nomenclature is the naming of these compounds as cycloamyloses.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, in embodiments having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantine, norbornane, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})C(=O)N(R^{15})_2$, $-R^{16}-N(R^{15})S(=O)_tR^{15}$ (where t is 1 or 2), $-R^{16}-S(=O)_tOR^{15}$ (where t is 1 or 2), $-R^{16}-S(=O)_pR^{15}$ (where p is 0, 1 or 2), and $-R^{16}-S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"Cycloalkylalkyl" refers to a radical of the formula $-R_aR_e$ where $R_a$ is an alkyl radical as defined above and $R_e$ is a cycloalkyl radical as defined above. The alkyl radical and the cycloalkyl radical may be optionally substituted as defined above.

"Cycloalkylalkenyl" refers to a radical of the formula $-R_cR_e$ where $R_c$ is an alkenyl radical as defined above and $R_e$ is a cycloalkyl radical as defined above. The alkenyl radical and the cycloalkyl radical may be optionally substituted as defined above.

"Cycloalkylalkynyl" refers to a radical of the formula $-R_dR_e$ where $R_d$ is an alkynyl radical as defined above and $R_e$ is a cycloalkyl radical as defined above. The alkynyl radical and the cycloalkyl radical may be optionally substituted as defined above.

"Guanidinyl" refers to a radical of the formula $(R_z)_2N-C(=NR_z)-N(R_z)_2$ wherein each $R_z$ is independently a direct bond, hydrogen, an alkyl, alkenyl, alkynyl, aryl, aralkyl, cycloalkyl, cycloalkylalkyl, heterocyclyl, heteroaryl, heteroarylalkyl as defined herein.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Haloalkynyl" refers to an alkynyl radical, as defined above, that is substituted by one or more halo radicals, as defined above. The alkynyl part of the haloalkyl radical may be optionally substituted as defined above for an alkynyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azepinyl, 2,5-diazabicyclo[2.2.1]heptan-2-yl, hexahydro-1H-1,4-diazepinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxiranyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$, —$R^{16}$—$N(R^{15})_2$, —$R^{16}$—$C(=O)R^{15}$ —$R^{16}$—$C(=O)OR^{15}$, —$R^{16}$—$C(=O)N(R^{15})^2$, —$R^{16}$—$N(R^{15})C(=O)OR^{15}$, —$R^{16}$—$N(R^{15})C(=O)R^{15}$, —$R^{16}$—$N(R^{15})C(=O)N(R^{15})_2$, —$R^{16}$—$N(R^{15})S(=O)_tR^{15}$ (where t is 1 or 2), —$R^{16}$—$S(=O)_tOR^{15}$ (where t is 1 or 2), —$R^{16}$—$S(=O)_pR^{15}$ (where p is 0, 1 or 2), and —$R^{16}$—$S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula —$R_aR_f$ where $R_a$ is an alkyl radical as defined above and $R_f$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heterocyclylalkenyl" refers to a radical of the formula —$R_cR_f$ where $R_c$ is an alkenyl radical as defined above and $R_f$ is a heterocyclyl radical as defined above, and if the heterocyclyl is a nitrogen-containing heterocyclyl, the heterocyclyl may be attached to the alkenyl radical at the nitrogen atom. The alkenyl part of the heterocyclylalkenyl radical may be optionally substituted as defined above for an alkenyl group. The heterocyclyl part of the heterocyclylalkenyl radical may be optionally substituted as defined above for a heterocyclyl group.

"Heterocyclylalkynyl" refers to a radical of the formula —$R_dR_f$ where $R_d$ is an alkynyl radical as defined above and $R_f$ is a heterocyclyl radical as defined above, and if the heterocyclyl is a nitrogen-containing heterocyclyl, the heterocyclyl may be attached to the alkynyl radical at the nitrogen atom. The alkynyl part of the heterocyclylalkynyl radical may be optionally substituted as defined above for an alkynyl group. The heterocyclyl part of the heterocyclylalkynyl radical may be optionally substituted as defined above for a heterocyclyl group.

"Heteroaryl" refers to a 3- to 18-membered fully or partially aromatic ring radical which consists of one to thirteen carbon atoms and from one to six heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; the nitrogen, carbon or sulfur atoms in the heteroaryl radical may be optionally oxidized; and the nitrogen atom may be optionally quaternized. Examples include, but are not limited to, acridinyl, benzimidazolyl, benzindolyl, benzodioxolyl, benzofuranyl, benzooxazolyl, benzothiazolyl, benzothiadiazolyl, benzo[b][1,4]dioxepinyl, benzo-[1,2,5]-oxadiazolyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrazolyl, pyridinyl, pyrazinyl, pyrimidinyl, pyridazinyl, pyrrolyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, oxo, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$, —$R^{16}$—$N(R^{15})_2$, —$R^{16}$—$C(=O)R^{15}$, —$R^{16}$—$C(=O)OR^{15}$, —$R^{16}$—$C(=O)N(R^{15})_2$, —$R^{16}$—$N(R^{15})C(=O)OR^{15}$, —$R^{16}$—$N(R^{15})C(=O)R^{15}$, —$R^{16}$—$N(R^{15})C(=O)N(R^{15})_2$, —$R^{16}$—$N(R^{15})S(=O)_tR^{15}$ (where t is 1 or 2), —$R^{16}$—$S(=O)_tOR^{15}$ (where t is 1 or 2), —$R^{16}$—$S(=O)_pR^{15}$ (where p is 0, 1 or 2), and —$R^{16}$—$S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_aR_g$ where $R_a$ is an alkyl radical as defined above and $R_g$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —$R_cR_g$ where $R_c$ is an alkenyl radical as defined above and $R_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Heteroarylalkynyl" refers to a radical of the formula —R$_d$R$_g$ where R$_d$ is an alkynyl radical as defined above and R$_g$ is a heteroaryl radical as defined above. The heteroaryl part of the heteroarylalkynyl radical may be optionally substituted as defined above for a heteroaryl group. The alkynyl part of the heteroarylalkynyl radical may be optionally substituted as defined above for an alkynyl group.

"Hydroxyalkyl" refers to an alkyl radical, as defined above, substituted by one or more hydroxy (—OH) groups. If the hydroxyalkyl radical is attached to a hetero atom (e.g., oxygen or nitrogen), a hydroxy group can not be attached to a carbon in the alkyl group which is directly attached to the hetero atom.

"Hydroxyiminoalkyl" refers to an alkyl radical, as defined above, substituted by a hydroxyimino (═NOH) group.

"Polymorph" refers to a polymorphic form of the compounds of the present disclosure. Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

"Prodrug" is meant to indicate a compound that may be converted under physiological conditions or by solvolysis to a biologically active compound of the present disclosure. Thus, the term "prodrug" refers to a metabolic precursor of a compound of the present disclosure that is pharmaceutically acceptable. A prodrug may be inactive when administered to a subject in need thereof, but is converted in vivo to an active compound of the present disclosure. Prodrugs are typically rapidly transformed in vivo to yield the parent compound of the present disclosure, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers, which release the active compound of the present disclosure in vivo when such prodrug is administered to a mammalian subject. Prodrugs of a compound of the present disclosure may be prepared by modifying functional groups present in the compound of the present disclosure in such a way that the modifications are cleaved, either in routine manipulation or in vivo, to the parent compound of the present disclosure. Prodrugs include compounds of the present disclosure wherein a hydroxy, amino or mercapto group is bonded to any group that, when the prodrug of the compound of the present disclosure is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the present disclosure and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. In embodiments, for purposes of this disclosure, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. In embodiments, inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases are isopropylamine, diethylamine, ethanolamine, trimethylamine, dicyclohexylamine, choline and caffeine.

A "pharmaceutical composition" refers to a formulation of a compound of the present disclosure and a medium generally accepted in the art for the delivery of the biologically active compound to mammals, for example, humans. Such a medium includes all pharmaceutically acceptable carriers, diluents or excipients.

"Solvate" refers to an aggregate that comprises one or more molecules of a compound of the present disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the present disclosure may be true solvates, while in other cases, the compound of the present disclosure may merely retain adventitious water or be a mixture of water plus some adventitious solvent.

"Therapeutically effective amount" refers to that amount of a compound of the present disclosure that, when administered to a mammal, such as a human, is sufficient to effect treatment, as defined below, of a disease or condition of interest in the mammal, such as a human. The amount of a compound of the present disclosure which constitutes a "therapeutically effective amount" will vary depending on, e.g., the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy, but it can be determined routinely by one of ordinary skill in the art having regard to his own knowledge and to this disclosure.

"Treating" or "treatment" as used herein covers the treatment of the disease or condition of interest in a mammal, such as a human, having the disease or condition of interest, and includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the present disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as for example, but not limited to, HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present disclosure includes tautomers of any said compounds.

Pharmaceutical Compositions and Administration

Administration of the compounds of the present disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the present disclosure in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the present disclosure, or a pharmaceutically acceptable salt thereof, for treatment of a disease or condition of interest in accordance with the teachings of this disclosure.

A pharmaceutical composition of the present disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, particular compositions contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present disclosure, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a particularly useful adjuvant. An injectable pharmaceutical composition is useful when sterile.

A liquid pharmaceutical composition of the present disclosure intended for either parenteral or oral administration should contain an amount of a compound of the present disclosure such that a suitable dosage will be obtained. Typically, this amount is at least 0.01% of a compound of the present disclosure in the composition. When intended for oral administration, this amount may be varied to be between 0.1 and about 70% of the weight of the composition. Some oral pharmaceutical compositions contain between about 4% and about 50% of the compound of the present disclosure. Some pharmaceutical compositions and preparations according to the present disclosure are prepared so that a parenteral dosage unit contains between 0.01 to 10% by weight of the compound prior to dilution.

The pharmaceutical composition of the present disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present disclosure from about 0.1 to about 10% w/v (weight per unit volume).

The pharmaceutical composition of the present disclosure may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present disclosure in solid or liquid form may include an agent that binds to the compound of the present disclosure and thereby assists in the delivery of the compound. Suitable agents that may act in this capacity include a monoclonal or polyclonal antibody, a protein or a liposome.

The pharmaceutical composition of the present disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine suitable aerosols.

The pharmaceutical compositions of the present disclosure may be prepared by methodology well known in the pharmaceutical art. For example, a pharmaceutical composition intended to be administered by injection can be prepared by combining a compound of the present disclosure with sterile, distilled water so as to form a solution. A surfactant may be added to facilitate the formation of a homogeneous solution or suspension. Surfactants are compounds that non-covalently interact with the compound of the present disclosure so as to facilitate dissolution or homogeneous suspension of the compound in the aqueous delivery system.

The compounds of the present disclosure, or their pharmaceutically acceptable salts, are administered in a therapeutically effective amount, which will vary depending upon a variety of factors and can be determined routinely by one of ordinary skill in the art. Generally, a therapeutically effective daily dose is (for a 70 kg mammal) from about 0.001 mg/kg (i.e., 0.7 mg) to about 100 mg/kg (i.e., 7.0 gm); in embodiments a therapeutically effective dose is (for a 70 kg mammal) from about 0.01 mg/kg (i.e., 7 mg) to about 50 mg/kg (i.e., 3.5 gm); in some embodiments a therapeutically effective dose is (for a 70 kg mammal) from about 1 mg/kg (i.e., 70 mg) to about 25 mg/kg (i.e., 1.75 gm).

Compounds of the present disclosure, or pharmaceutically acceptable derivatives thereof, may also be administered simultaneously with, prior to, or after administration of one or more other therapeutic agents. Such combination therapy includes administration of a single pharmaceutical dosage formulation which contains a compound of the present disclosure and one or more additional active agents, as well as administration of the compound of the present disclosure and each active agent in its own separate pharmaceutical dosage formulation. For example, a compound of the present disclosure and the other active agent can be administered to the patient together in a single oral dosage composition such as a tablet or capsule, or each agent can be administered in separate oral dosage formulations. Where separate dosage formulations are used, the compounds of the present disclosure and one or more additional active agents can be administered at essentially the same time, i.e., concurrently, or at separately staggered times, i.e., sequentially; combination therapy is understood to include all these regimens.

Examples of classes of agents which may be utilized in combination with the compounds described herein include, without limitation, antimicrobials, analgesics, antipyretics, anesthetics, antiepileptics, antihistamines, anti-asthmatics, anticholesterols, CFTR modulators, CNS drugs, antidepressants, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, enzymes, and combinations thereof.

Utility of the Compounds Described Herein

The compounds of the present disclosure are inhibitors of $LTA_4$-h activity and are therefore useful in treating diseases and disorders which are ameliorated by the inhibition of $LTA_4$-h activity. Such diseases and conditions include inflammatory and autoimmune disorders and pulmonary and respiratory tract inflammation.

Accordingly, the compounds are useful in the treatment of the following diseases or disorders in mammals, particularly humans: acute or chronic inflammation, anaphylactic reactions, allergic reactions, allergic contact dermatitis, allergic rhinitis, chemical and non-specific irritant contact dermatitis, urticaria, atopic dermatitis, psoriasis, fistulas associated with Crohn's disease, pouchitis, septic or endotoxic shock, hemorrhagic shock, shock-like syndromes, capillary leak syndromes induced by immunotherapy of cancer, acute respiratory distress syndrome, traumatic shock, immune- and pathogen-induced pneumonias, immune complex-mediated pulmonary injury and chronic obstructive pulmonary disease, inflammatory bowel diseases (including ulcerative colitis, Crohn's disease and post-surgical trauma), gastrointestinal ulcers, diseases associated with ischemia-reperfusion injury (including acute myocardial ischemia and infarction, acute renal failure, ischemic bowel disease and acute hemorrhagic or ischemic stroke), immune-complex-mediated glomerulonephritis, autoimmune diseases (including insulin-dependent diabetes mellitus, multiple sclerosis, rheumatoid arthritis, osteoarthritis and systemic lupus erythematosus), acute and chronic organ transplant rejection, transplant arteriosclerosis and fibrosis, cardiovascular disorders (including hypertension, atherosclerosis, aneurysm, critical leg ischemia, peripheral arterial occlusive disease and Reynaud's syndrome), complications of diabetes (including diabetic nephropathy, neuropathy and retinopathy), ocular disorders (including macular degeneration and glaucoma), neurodegenerative disorders (including delayed neurodegeneration in stroke, Alzheimer's disease, Parkinson's disease, encephalitis and HIV dementia), inflammatory and neuropathic pain including arthritic pain, periodontal disease including gingivitis, ear infections, migraine, benign prostatic hyperplasia, and cancers (including, but not limited to, leukemias and lymphomas, prostate cancer, breast cancer, lung cancer, malignant melanoma, renal carcinoma, head and neck tumors and colorectal cancer).

The compounds are also useful in treating folliculitis induced by inhibitors of epidermal growth factor (EGF) or epidermal growth factor receptor (EGFR) kinase used in the treatment of solid tumors. Clinical trials have revealed folliculitis (inflammation of the hair follicle manifested by severe acne-like skin rash on the face, chest and upper back) as a major dose-limiting side effect of such treatments. Such folliculitis is associated with an infiltration of neutrophils suggesting products secreted by activated neutrophils to be the cause of the inflammation. The compounds of the present disclosure inhibit neutrophil or eosinophil-mediated inflammation, and are therefore useful in treating such folliculitis, thereby improving the quality of life of the treated cancer patients but also allowing for the increase of the dosage of the EGF inhibitor or EGFR kinase inhibitor or the extension of the duration of the treatment, resulting in improved efficacy of the desired inhibitor.

The compounds are also useful in the treatment of pulmonary and respiratory inflammation disorders in mammals, particularly humans, including, but not limited to, asthma, chronic bronchitis, cystic fibrosis, bronchiolitis, bronchiolitis obliterans (including such with organizing pneumonia), allergic inflammation of the respiratory tract (including rhinitis and sinusitis), eosinophilic granuloma, pneumonias, pulmonary fibroses, pulmonary manifestations of connective tissue diseases, acute or chronic lung injury, chronic obstructive pulmonary diseases, adult respiratory distress syndrome, and other non-infectious inflammatory disorders of the lung characterized by eosinophil infiltration.

For example, the compounds of the present disclosure are useful in the inhibition of: eosinophil-mediated inflammation of the lung or tissues; neutrophil-mediated inflammation of the lung; lymphocyte-mediated inflammation of the lung; airway hyper-responsiveness; and airway and vascular inflammation.

The compounds are also useful in the treatment of myocardial infarction or susceptibility to myocardial infarction in mammals, particularly humans, transient ischemic attack, transient monocular blindness, stroke or susceptibility of stroke, claudication, peripheral arterial occlusive disease or susceptibility to peripheral arterial occlusive disease, and acute coronary syndrome (such as unstable angina, non-ST-elevation myocardial infarction or ST-elevation myocardial infarction). The compounds are also useful in the methods for reducing the risk of myocardial infarction, stroke or peripheral arterial occlusive disease in mammals and reducing the risk of a second myocardial infarction or stroke.

The compounds are also useful in the treatment of atherosclerosis in mammals, particularly humans who require treatment (such as angioplasty, stents, coronary artery bypass graft) in order to restore blood flow in the arteries (such as in the coronary arteries).

The compounds are also useful in inhibiting the synthesis of leukotriene $B_4$ in both in vitro and in vivo assays.

Testing of the Compounds Described Herein

Testing of the compounds described herein including the following three (3) assays: a $LTA_4$ hydrolase homogeneous time resolved fluorescence assay; a peptidase assay; and, a whole blood assay.

$LTA_4$ Hydrolase Homogeneous Time Resolved Fluorescence Assay

Compounds of the invention were tested in the $LTA_4$ hydrolase homogeneous time resolved fluorescence (HTRF) assay to determine their ability to inhibit the hydrolysis of $LTA_4$ to $LTB_4$. The assay analyzes the amount of $LTB_4$ produced.

$LTA_4$ HTRF assay is a two-step assay involving enzymatic conversion of $LTA_4$ to $LTB_4$, and subsequent quantification of $LTB_4$, product with HTRF assay.

The enzymatic conversion of $LTA_4$ to $LTB_4$ was performed in 384-well plates at ambient temperature in a reaction mixture containing 50 mM HEPES (pH 7.5), 0.5% BSA (fatty acid free), 18 nM recombinant human $LTA_4$ hydrolase, 150 nM $LTA_4$, 1% DMSO in the absence or presence of a compound of the invention. Reaction was stopped after 10 minutes incubation by diluting the incubation mixture 10-fold in 50 mM phosphate, 0.1% casein buffer (pH 7.0).

$LTB_4$ formed was quantified with the HTRF assay in which free $LTB_4$ competes with $LTB_4$-XL665 conjugate (acceptor) for anti-$LTB_4$ monoclonal antibody labeled with Europium cryptate (donor), thereby inhibiting the fluorescence energy transfer.

The $LTB_4$ HTRF 384-well assay was carried out by incubating $LTB_4$ samples or standards with $LTB_4$-XL665 conjugate (7.5 ng/well) and anti-$LTB_4$ monoclonal antibody-Europium cryptate conjugate (0.5 ng/well) in 50 mM phosphate, 0.4 M KF and 0.1% casein, buffer (pH 7.0) for two hours at ambient temperature. Plates were read in a RubyStar plate reader (BmG Labtechnologies Inc., NC) simultaneously at 620 nm and 665 nm to obtain signal ratios of 665 nm/620 nm. Results of energy transfer were expressed as delta F (%) which equaled [(signal ratio of sample−signal ratio of negative control)/(signal ratio of negative control)]×100%. Negative controls were control samples without $LTB_4$ or $LTB_4$-XL665.

Sample $LTB_4$ concentrations were calculated from the $LTB_4$ standard curve using the 4-parameter fit equation. For determination $IC_{50}$ values for a particular compound of the invention, eight serially diluted compound concentrations (at 1:3.16 dilution) were used in this assay. Controls without a compound of the invention or with a reference compound were run parallel in the same assay plate.

Compounds of the invention, when tested in this assay, demonstrated the ability to inhibit $LTA_4$ hydrolase activity at $IC_{50}$ values of less than 100 μM, in some embodiments less than 1 μM, in some embodiments less than 100 nM, in some embodiments less than 75 nM, in some embodiments less than 50 nM, in some embodiments less than 25 nM, in some embodiments less than 10 nM, in some embodiments less than 5 nM.

In embodiments, the compounds of the invention, when tested in this assay, demonstrated the ability to inhibit $LTA_4$ hydrolase activity at $IC_{50}$ values from 0.01 nM to 10 μM, in embodiments from 0.1 nM to 100 nM, in some embodiments from 0.5 nM to 75 nM, from some embodiments from 1 nM to 50 nM, in some embodiments from 5 nM to 25 nM.

Peptidase Assay

Inhibition of peptidase activity was measured for the compounds of the invention by using methods similar to those described in Kull, F. et al., *The Journal of Biological Chemistry* 1999, 274 (49): 34683-34690. In particular, the peptidase activity of the compounds was measured by inhibition of the hydrolysis of L-alanine-p-nitroanilide to L-alanine and highly colored nitro-aniline as set forth below in the following reaction

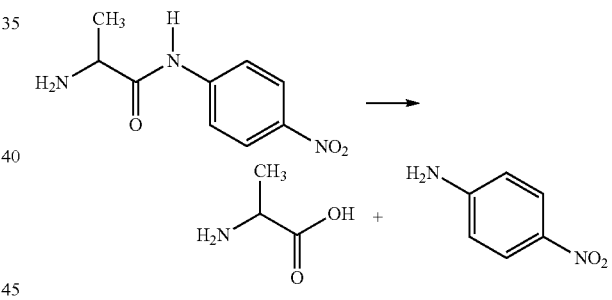

In brief, the enzyme (29 nM) was incubated with L-alanine-p-nitroanilide (1 mM) in 50 mM HEPES (pH 7.5), 100 mM KCL, 1% DMSO in the absence or presence of a compound of the invention for 1 hour at ambient temperature. Reaction was terminated by addition of acetic acid (1%). Formation of colored nitro-aniline was measured by the increase in absorbance at 405 nm in a Victor 2 plate reader (Wallac). Spontaneous hydrolysis of the substrate was corrected for by subtracting the absorbance of control incubations without enzyme.

In embodiments, the compounds of the invention, when tested in this assay, demonstrated the ability to inhibit peptidase activity at IC50 values of less than 100 μM, in some embodiments less than 1 μM, in some embodiments less than 100 nM, in some embodiments less than 75 nM, in some embodiments less than 50 nM, in some embodiments less than 25 nM, in some embodiments less than 10 nM, in some embodiments less than 5 nM.

In embodiments, the compounds of the invention, when tested in this assay, demonstrated the ability to inhibit peptidase activity at IC50 values from 0.01 nM to 10 μM, in some embodiments from 0.1 nM to 100 nM, in some embodiments from 0.5 nM to 75 nM, from some embodiments from 1 nM to 50 nM, in some embodiments from 5 nM to 25 nM, in some embodiments from 0.1 nM to 5 nM, in some embodiments from 1 nM to 3 nM.

Compounds of the invention, when tested in both LTA$_4$ hydrolase and/or peptidase assays described herein, demonstrated the ability to inhibit LTA$_4$ hydrolase activity and/or peptidase activity at IC$_{50}$ values of less than 100 μM, in some embodiments less than 1 μM, in some embodiments less than 100 nM, in some embodiments less than 75 nM, in some embodiments less than 50 nM, in some embodiments less than 25 nM, in some embodiments less than 10 nM.

Compounds of the invention, when tested in both the LTA$_4$ hydrolase and/or peptidase assays described herein, demonstrated the ability to inhibit LTA$_4$ hydrolase activity and/or peptidase activity at IC$_{50}$ values from 0.01 nM to 10 μM, in embodiments from 0.1 nM to 100 nM, in some embodiments from 0.5 nM to 75 nM, in some embodiments from 1 nM to 50 nM, in some embodiments from 1 nM to 25 nM, in some embodiments from 1 nM to 10 nM Whole Blood Assay Compounds of the invention were tested for their ability as inhibitors of LTA$_4$ hydrolase in a whole blood assay using human, mouse, rat or dog whole blood in a manner similar to that described in Penning, T. D. et al., *J. Med. Chem.* (2000), 43(4): 721-735. In this assay, compounds were tested for their ability to inhibit LTB$_4$ release upon stimulation with calcium ionophore. The LTB$_4$ levels in supernatants were measured by ELISA.

Compounds of the invention inhibited the release or production of LTB$_4$ upon addition of calcium ionophore in a dose-dependent manner from whole blood in all species tested.

In embodiments, the compounds of the invention, when tested in this assay, demonstrated the ability to inhibit production of LTB$_4$ in whole blood at IC$_{50}$ values of less than 100 μM, in some embodiments less than 10 μM, in some embodiments less than 1 uM, in some embodiments less than 500 nM, in some embodiments less than 250 nM, in some embodiments less than 125 nM, in some embodiments less than 100 nM, in some embodiments less than 75 nM.

In embodiments, the compounds of the invention, when tested in this assay, demonstrated the ability to inhibit release of LTB$_4$ at IC$_{50}$ values from 0.01 nM to 10 μM, in some embodiments from 0.1 nM to 1 uM, in some embodiments from 0.5 nM to 500 nM, from some embodiments from 1 nM to 250 nM, in some embodiments from 5 nM to 125 nM, in some embodiments from 50 nM to 100 nM.

Compounds of the invention, when tested in all three assays described herein, i.e., the LTA$_4$ hydrolase assay, the peptidase assay, and/or the whole blood assay, demonstrated the ability to inhibit LTA$_4$ hydrolase activity, peptidase activity and/or the production of LTB$_4$ in whole blood at IC$_{50}$ values of less than 100 μM, in some embodiments less than 1 μM, in some embodiments less than 100 nM, in some embodiments less than 75 nM.

Compounds of the invention, when tested in both the LTA$_4$ hydrolase and/or the peptidase assays described herein, demonstrated the ability to inhibit LTA$_4$ hydrolase activity and/or peptidase activity and the production of LTB$_4$ in whole blood at IC$_{50}$ values from 0.01 nM to 10 μM, in embodiments from 0.1 nM to 100 nM, in some embodiments from 0.5 nM to 75 nM, in some embodiments from 1 nM to 100 nM, in some embodiments from 2 nM to 75 nM.

Exemplary Embodiments

The present disclosure describes compounds of Formula (I), as single stereoisomers or as mixtures of stereoisomers, and the pharmaceutically acceptable salts, solvates, polymorphs, clathrates, ammonium ions, N-oxides or prodrugs thereof, as set forth above in the Summary.

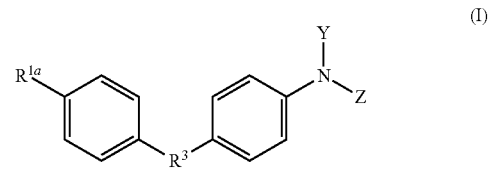

(I)

wherein R$^{1a}$, R$^3$, Y, and Z are as described above in the Summary.

In embodiments, the compounds of Formula (I) include those wherein R$^3$ is —O—, Z is

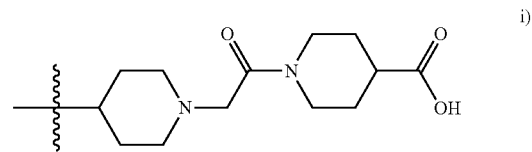 [SMILES: *C1CCN(CC(=O)N2CCC(C(=O)O)CC2)CC1]

i)

and the remaining substituents, such as R$^{1a}$ and Y are as described in the Summary.

In embodiments, the compounds of Formula (I) include those wherein R$^3$ is —O—, Z is

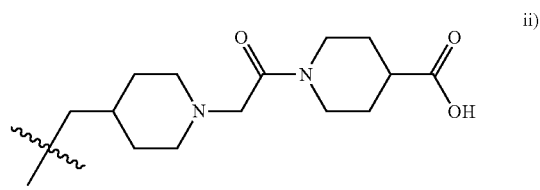 [SMILES: *CC1CCN(CC(=O)N2CCC(C(=O)O)CC2)CC1]

ii)

and the remaining substituents, such as R$^{1a}$ and Y are as described in the Summary.

In embodiments, the compounds of Formula (I) include those wherein R$^3$ is —O—, Z is

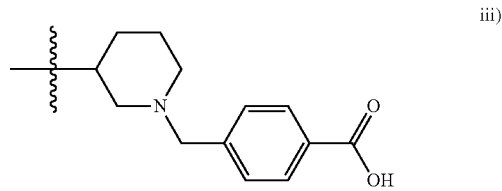 [SMILES: *C1CCCN(Cc2ccc(C(=O)O)cc2)C1]

iii)

and the remaining substituents, such as R$^{1a}$ and Y are as described in the Summary.

In embodiments, the compounds of Formula (I) include those wherein R$^3$ is —O—, Z is

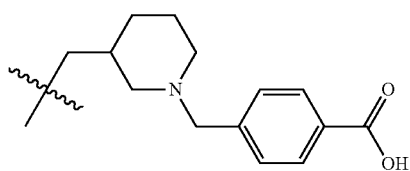

iv)

and the remaining substituents, such as $R^{1a}$ and Y are as described in the Summary.

In embodiments, the compounds of Formula (I) include those wherein $R^{1a}$ is halo, Z is

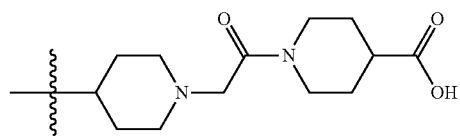

i)

and the remaining substituents, such as $R^3$ and Y are as described in the Summary.

In embodiments, the compounds of Formula (I) include those wherein $R^{1a}$ is halo, Z is

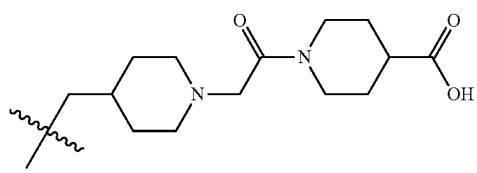

ii)

and the remaining substituents, such as $R^3$ and Y are as described in the Summary.

In embodiments, the compounds of Formula (I) include those wherein $R^{1a}$ is halo, Z is

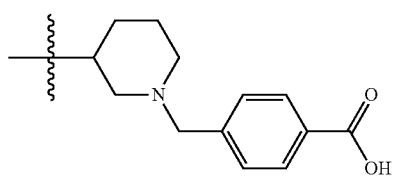

iii)

and the remaining substituents, such as $R^3$ and Y are as described in the Summary.

In embodiments, the compounds of Formula (I) include those wherein $R^{1a}$ is halo, Z is

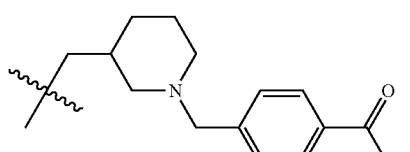

iv)

and the remaining substituents, such as $R^3$ and Y are as described in the Summary.

In embodiments, the compounds of Formula (I) include those wherein $R^{1a}$ is an optionally substituted heteroaryl, Z is

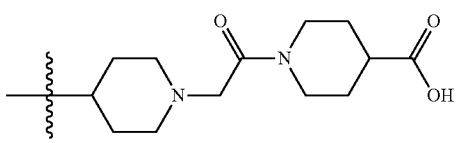 [SMILES: *C1CCN(CC(=O)N2CCC(C(=O)O)CC2)CC1]

i)

and the remaining substituents, such as $R^3$ and Y are as described in the Summary.

In embodiments, the compounds of Formula (I) include those wherein $R^{1a}$ is an optionally substituted heteroaryl, Z is

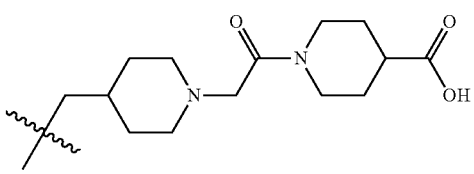

ii)

and the remaining substituents, such as $R^3$ and Y are as described in the Summary.

In embodiments, the compounds of Formula (I) include those wherein $R^{1a}$ is an optionally substituted heteroaryl, Z is

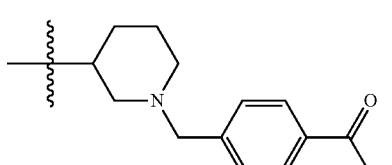

iii)

and the remaining substituents, such as $R^3$ and Y are as described in the Summary.

In embodiments, the compounds of Formula (I) include those wherein $R^{1a}$ is an optionally substituted heteroaryl, Z is

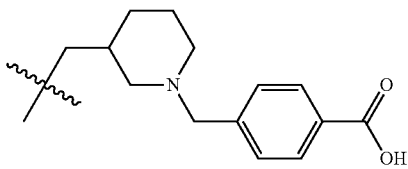

iv)

and the remaining substituents, such as $R^3$ and Y are as described in the Summary.

In embodiments, the compounds of Formula (I) include those wherein $R^{1a}$ is an optionally substituted heteroaryl, Y is a hydrogen, Z is

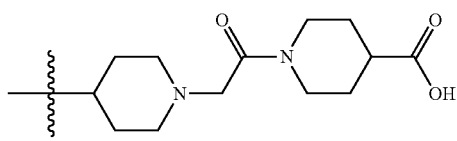 [SMILES: *C1CCN(CC(=O)N2CCC(C(=O)O)CC2)CC1]

and R³ is as described in the Summary.

In embodiments, the compounds of Formula (I) include those wherein R¹ᵃ is an optionally substituted heteroaryl, Y is a hydrogen, Z is

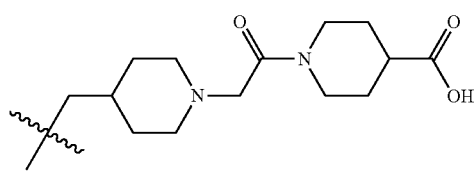

and R³ is as described in the Summary.

In embodiments, the compounds of Formula (I) include those wherein R¹ᵃ is an optionally substituted heteroaryl, Y is a hydrogen, Z is

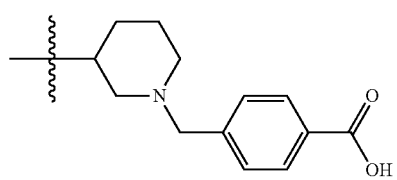

and R³ is as described in the Summary.

In embodiments, the compounds of Formula (I) include those wherein R¹ᵃ is an optionally substituted heteroaryl, Y is a hydrogen, Z is

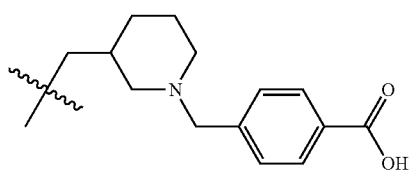

and R³ is as described in the Summary.

In additional embodiments, the compounds described herein may include those of Formula (I-A)

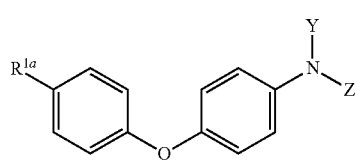

wherein

R¹ᵃ is hydrogen, halo, haloalkyl, haloalkenyl, haloalkynyl, hydroxyalkyl, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, —R¹³—OR¹⁰, —R¹³—C(=O)OR¹⁰, or —R¹³—C(=O)R¹⁰;

Y is hydrogen, halo, haloalkyl, haloalkenyl, haloalkynyl, hydroxyalkyl, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroarylalkyl optionally substituted heterocyclyl, or optionally substituted heterocyclylalkyl; and Z is

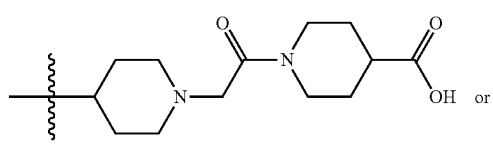

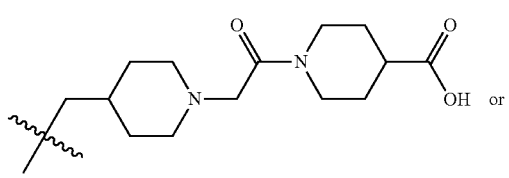

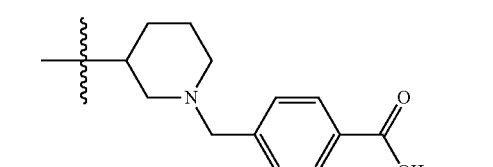

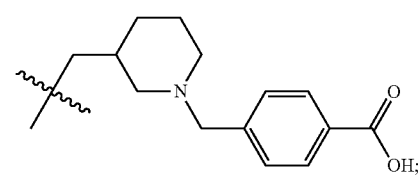

each R¹⁰ is independently hydrogen, haloalkyl, haloalkenyl, haloalkynyl, hydroxyalkyl, optionally substituted alkyl, optionally substituted alkenyl, optionally substituted alkynyl, optionally substituted aryl, optionally substituted aralkyl, optionally substituted heteroaryl, optionally substituted heteroarylalkyl, optionally substituted heterocyclyl, or optionally substituted heterocyclylalkyl;

each R¹³ is independently a direct bond, an optionally substituted straight or branched alkylene chain, an optionally substituted straight or branched alkenylene chain, or an optionally substituted straight or branched alkynylene chain as a single stereoisomer or as a mixture of stereoisomers;

or a pharmaceutically acceptable salt, solvate, polymorph, clathrate, ammonium ion, N-oxide or prodrug thereof.

In embodiments, the compounds of Formula (I-A) include some examples provided below in Table I.

TABLE I
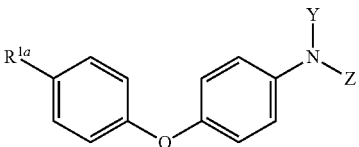
| $R^{1a}$ | Y | Z |
|---|---|---|
| H— | H— | 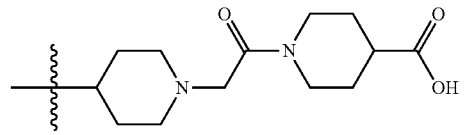 |
| Heteroaryl— | H— | 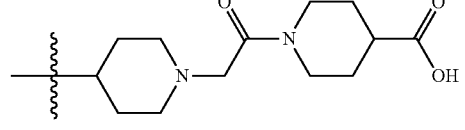 |
| 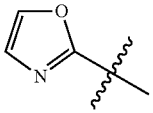 [SMILES: *c1ncco1] | H— | 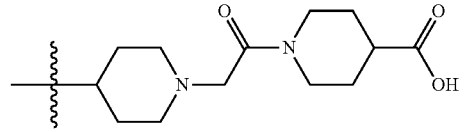 |
| Halo— | H— | 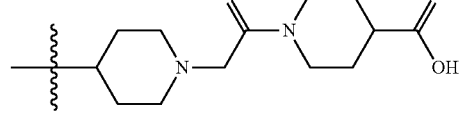 |
| Cl— | H— | 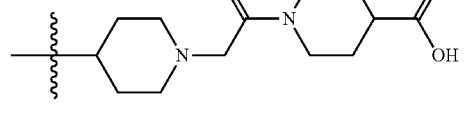 |
| H— | H— | 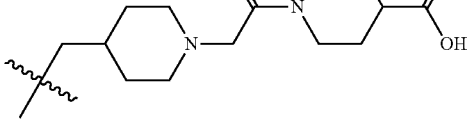 |
| Heteroaryl— | H— | 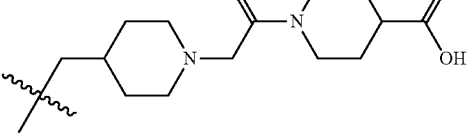 |
| 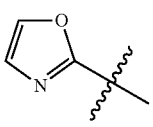 | H— | 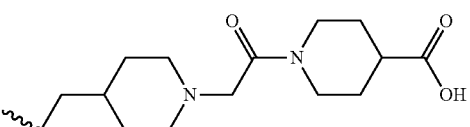 |
| Halo— | H— | 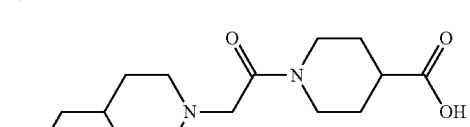 |

TABLE I-continued
| R$^{1a}$ | Y | Z |
|---|---|---|
| Cl— | H— | 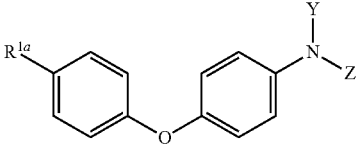 |
| H— | H— | 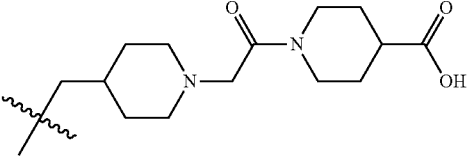 [SMILES: *CC1CCN(CC(=O)N2CCC(C(=O)O)CC2)CC1] |
| Heteroaryl— | H— | 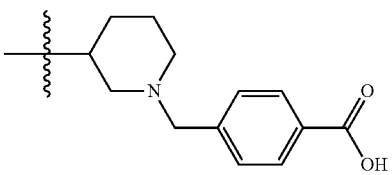 [SMILES: *C1CCCN(Cc2ccc(C(=O)O)cc2)C1] |
| 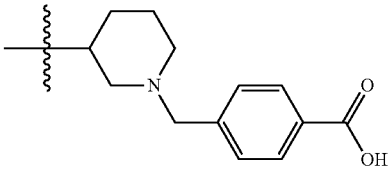 [SMILES: *C1CCCN(Cc2ccc(C(=O)O)cc2)C1] | H— | 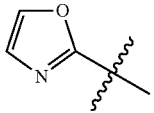 [SMILES: *c1ncco1] |
| Halo— | H— | 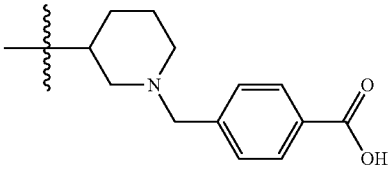 [SMILES: *C1CCCN(Cc2ccc(C(=O)O)cc2)C1] |
| Cl— | H— | 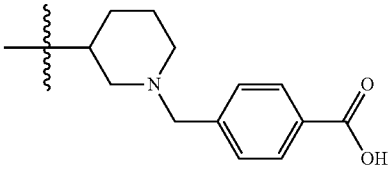 [SMILES: *C1CCCN(Cc2ccc(C(=O)O)cc2)C1] |
| H— | H— | 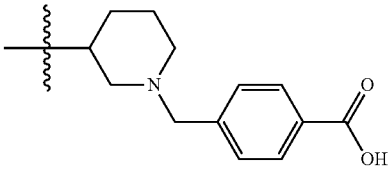 [SMILES: *C1CCCN(Cc2ccc(C(=O)O)cc2)C1] |

TABLE I-continued
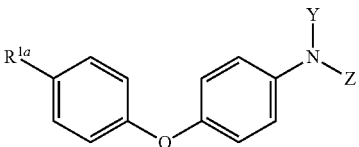
| R$^{1a}$ | Y | Z |
|---|---|---|
| Heteroaryl— | H— | 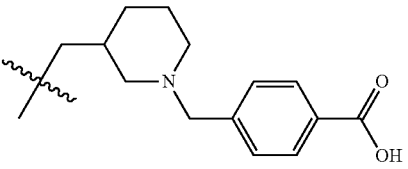 [SMILES: *CC1CCCN(Cc2ccc(C(=O)O)cc2)C1] |
| 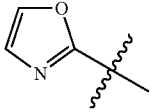 [SMILES: *c1ncco1] (oxazole) | H— | 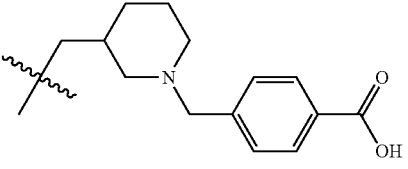 |
| Halo— | H— | 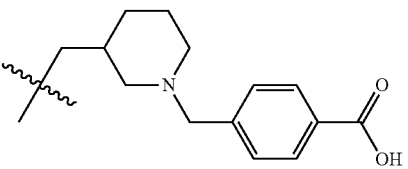 [SMILES: *CC1CCCN(Cc2ccc(C(=O)O)cc2)C1] |
| Cl— | H— | 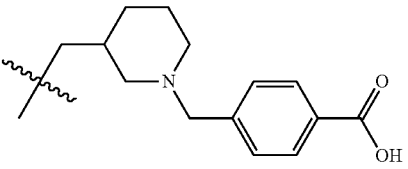 [SMILES: *CC1CCCN(Cc2ccc(C(=O)O)cc2)C1] |
In particular embodiments, compounds of Formula (I) include at least one of the following compounds in Table 2.
TABLE 2
| Compound | Hydrolase IC50 (nM) | Peptidase IC50 (nM) | Human Whole Blood IC50 (nM) |
|---|---|---|---|
| 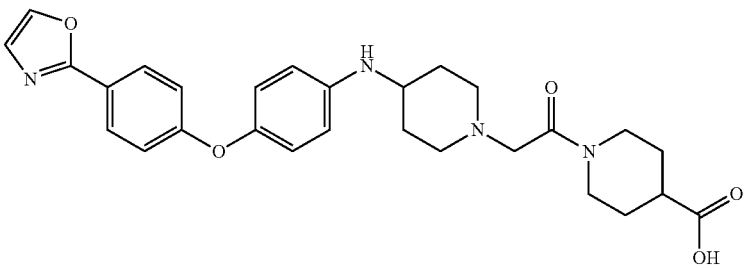 [SMILES: O=C(O)C1CCN(C(=O)CN2CCC(Nc3ccc(Oc4ccc(-c5ncco5)cc4)cc3)CC2)CC1] | 2.1 | 7.1 | 62 |

TABLE 2-continued

| Compound | Hydrolase IC50 (nM) | Peptidase IC50 (nM) | Human Whole Blood IC50 (nM) |
|---|---|---|---|
| 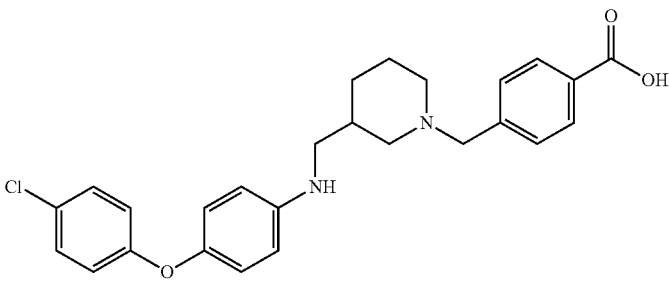 [SMILES: O=C(O)c1ccc(CN2CCCC(CNc3ccc(Oc4ccc(Cl)cc4)cc3)C2)cc1] | 1.8 | 22 | 100 |

In particular embodiments, compounds of Formula (I) include 4-((3-(((4-(4-chlorophenoxy)phenyl)amino)methyl)piperidin-1-yl)methyl)benzoic acid or 1-(2-(4-((4-(4-(ox-azol-2-yl)phenoxy)phenyl)amino)piperidin-1-yl)acetyl)piperidine-4-carboxylic acid.

While the compounds of the present disclosure are described with reference to specific embodiments, it should be understood by those skilled in the art that various changes may be made and equivalents may be substituted without departing from the true spirit and scope of the present disclosure.

Preparation of Compounds Described Herein

The following Reaction Schemes illustrate methods to make the compounds of Formula (I):

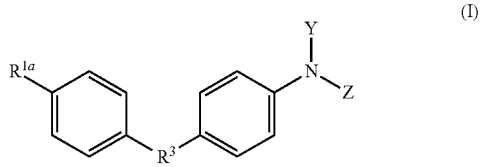

where $R^{1a}$, $R^3$, Y, and Z are described above in the Summary, as single stereoisomers or as mixtures of stereoisomers, and the pharmaceutically acceptable salts, solvates, clathrates, polymorphs, ammonium ions, N-oxides or prodrugs thereof. It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidine include t-butoxycarbonyl, benzyloxycarbonyl, and the like. Suitable protecting groups for mercapto include —C(=O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which may be known to one skilled in the art and as described herein It will also be appreciated by those skilled in the art, although such protected derivatives of compounds of this disclosure may not possess pharmacological activity as such, they may be administered to a mammal and thereafter metabolized in the body to form compounds of the present disclosure which are pharmacologically active. Such derivatives may therefore be described as "prodrugs". All prodrugs of compounds described herein are included within the scope of the present disclosure.

It is understood that one of ordinary skill in the art would be able to make the compounds described herein by methods similar to the methods described herein or by methods known to one of ordinary skill in the art. It is also understood that one of ordinary skill in the art would be able to make in a similar manner as described below other compounds of formula (I) not specifically illustrated below by using the appropriate starting components and modifying the parameters of the synthesis as needed. In general, compounds employed as initial starting materials in the synthesis of the compounds of the disclosure are well known and commercially available, e.g., from Sigma Aldrich, Lancaster Synthesis, Inc., Maybridge, Matrix Scientific, TCI, and Fluorochem USA, etc. To the extent that the compounds employed as initial starting materials are not commercially available, the compounds may be readily synthesized using specific references provided, or by standard procedures commonly employed by those of ordinary skill in the art and/or found in general references text (see, for example, *Comprehensive Organic Transformations*, VCH Publishers Inc., 1989; *Compendium of Organic Synthetic Methods*, Volumes 1-10, 1974-2002, Wiley Interscience; *Advanced Organic Chemistry: Reactions, Mechanisms, and Structure*, 5th edition, Wiley Interscience, 2001; *Advanced Organic Chemistry*, 4th Edition, Part B, Reactions and Synthesis, Kluwer Academic/Plenum Publishers, 2000, etc., and references cited therein).

In the following Reaction Scheme and examples, the following common abbreviations are used:
Boc for t-butoxycarbonyl
$CH_2Cl_2$ for dichloromethane
$ClCH_2CH_2Cl$ for 1,2-dichloroethane
DMF for N,N-dimethylformamide
$Et_2O$ for diethyl ether
$(iPr)_2NEt$ for Hunig's Base
MeCN for acetonitrile
MeOH for methanol
NaOH for sodium hydroxide
$NaBh(OAc)_3$ for sodium triacetoxyborohydride
$PH-NEt_2$ for diethyl aniline
TFA for trifluoroacetic acid Reaction Scheme I

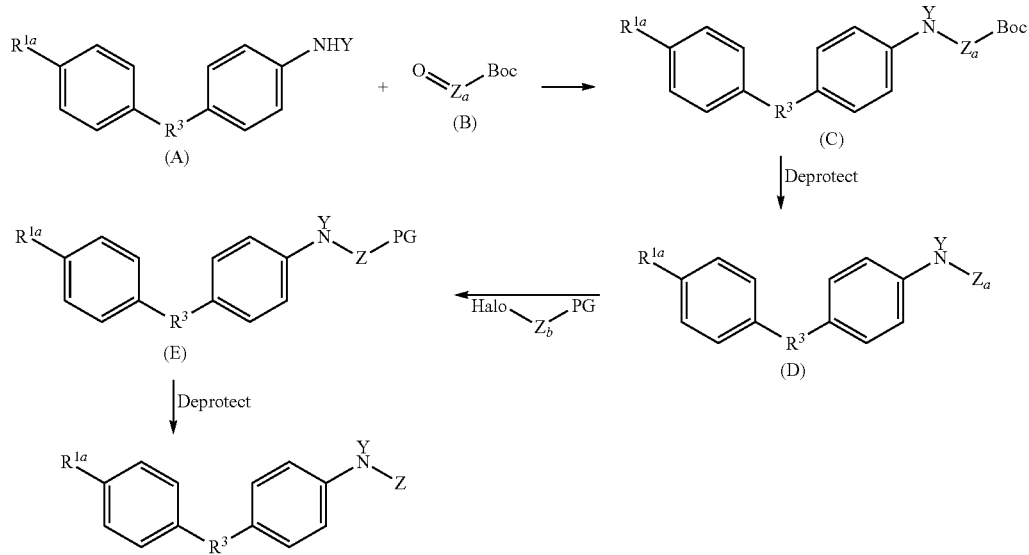

Compounds (A) and/or (B) are commercially available and/or can be prepared by methods known to one of ordinary skill in the art. In compounds of (A)-(E), each $R^{1a}$, $R^3$, and Y is as described in the Summary herein. In compounds of (B), $Z_a$ represents a first portion of Z. For example, in embodiments $Z_a$ represents an optionally substituted N-heterocyclyl, such as a piperidinyl, as a first portion of Z. ($Z_a$+$Z_b$=Z)

Compound (C) is protected with a pendant -Boc group. Compound (C) may be mixed with a strong acid, such as TFA, to remove -Boc thereby forming deprotected compound (D). Compound (D) is mixed with Halo-$Z_b$-PG, wherein Halo is often Bromine (Br—), PG stands for a Protective Group, such as methyl group, and $Z_b$ represents a second portion of Z. For example, in embodiments, $Z_b$ represents an optionally substituted aralkyl or an optionally substituted N-heterocyclyl, such as a piperidinyl, as a second portion of Z.

In embodiments, $Z_a$ of Scheme I represents

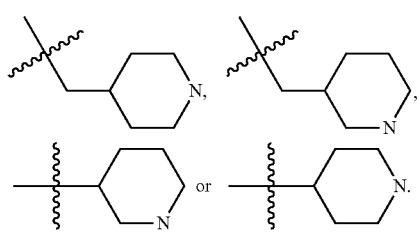

In embodiments, $Z_b$ of Scheme I represents

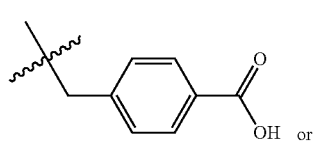

-continued

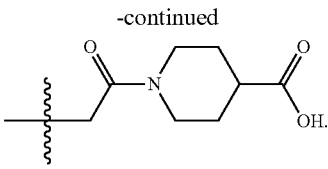

In embodiments, $Z_a$ of Scheme I represents

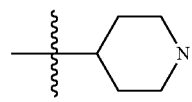

and $Z_b$ of Scheme I represents

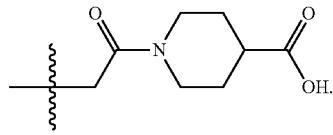 [SMILES: *CC(=O)N1CCC(C(=O)O)CC1]

In embodiments, $Z_a$ of Scheme I represents

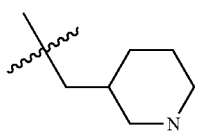 [SMILES: *CC1CCCNC1]

and $Z_b$ of Scheme I represents

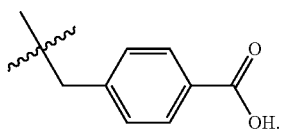 [SMILES: *Cc1ccc(C(=O)O)cc1]

It is understood that other compounds described herein and not specifically disclosed in the above Reaction Scheme may be similarly prepared with the appropriate starting materials.

Reaction Scheme II

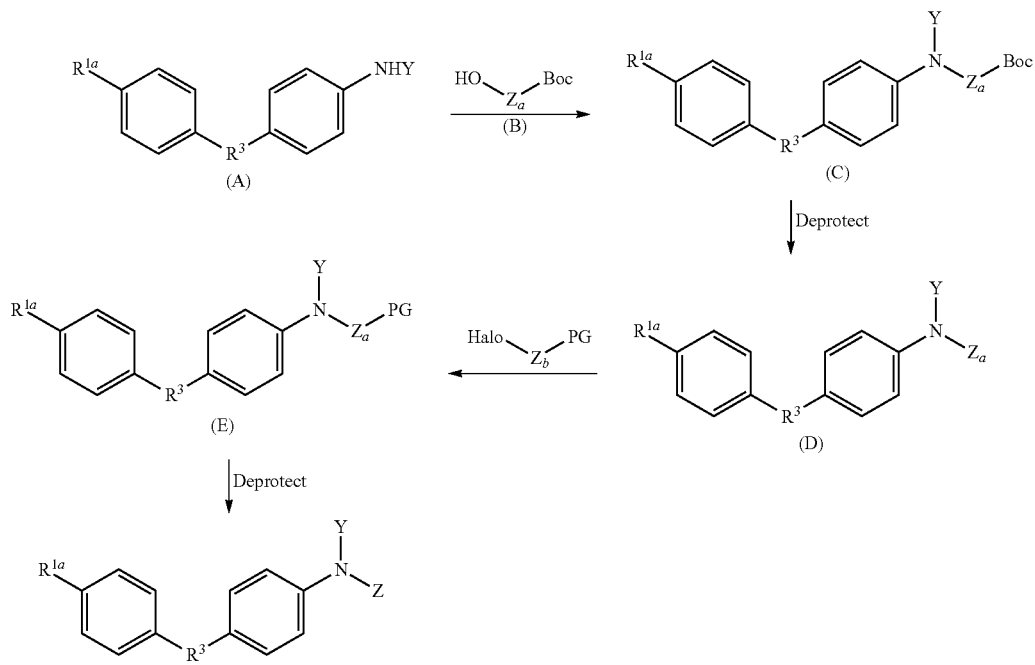

Compounds (A) and/or (B) are commercially available and/or can be prepared by methods known to one of ordinary skill in the art. In compounds of (A)-(E), each $R^{1a}$, $R^3$, and Y is as described in the Summary herein. In compounds of (B), $Z_a$ represents a first portion of Z. For example, in embodiments $Z_a$ represents an optionally substituted N-heterocyclyl, such as a piperidinyl, as a first portion of Z. ($Z_a + Z_b = Z$).

Compound (C) is protected with a pendant -Boc group. Compound (C) may be mixed with a strong acid, such as TFA, to remove -Boc thereby forming deprotected compound (D). Compound (D) is mixed with Halo-$Z_b$-PG, wherein Halo is often Bromine (Br—), PG stands for a Protective Group, such as methyl group, and $Z_b$ represents a second portion of Z. For example, in embodiments, $Z_b$ represents an optionally substituted aralkyl or an optionally substituted N-heterocyclyl, such as a piperidinyl, as a second portion of Z.

In embodiments, $Z_a$ of Scheme II represents

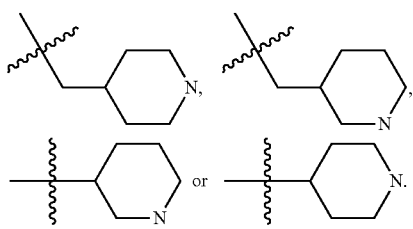

In embodiments, $Z_b$ of Scheme II represents

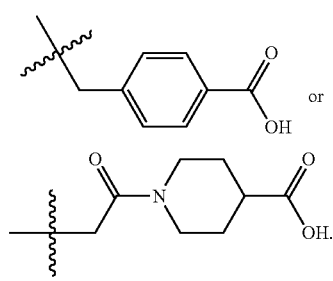

In embodiments, $Z_a$ of Scheme II represents

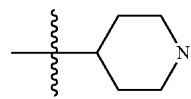

and $Z_b$ of Scheme II represents

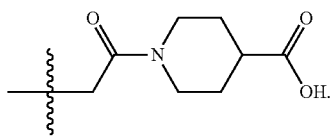 [SMILES: *CC(=O)N1CCC(C(=O)O)CC1]

In embodiments, $Z_a$ of Scheme II represents

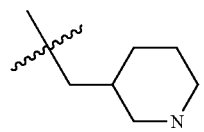

and $Z_b$ of Scheme II represents

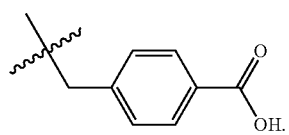 [SMILES: *Cc1ccc(C(=O)O)cc1]

It is understood that other compounds described herein and not specifically disclosed in the above Reaction Scheme may be similarly prepared with the appropriate starting materials.

All compounds of the present disclosure as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds described herein are intended to be within the scope of the present disclosure. Furthermore, all compounds of the present disclosure which contain an ester group can be converted to the corresponding acid by methods known to one skilled in the art or by methods described herein.

To prepare the cyclodextrin clathrates described herein, the compounds of formula (I), as defined above in the Summary, can be dissolved in a pharmacologically acceptable solvent, e.g., in an alcohol, preferably ethanol, in a ketone, e.g., acetone or in an ether, e.g., diethyl ether, and mixed with aqueous solutions of α-cyclodextrin, β-cyclodextrin or γ-cyclodextrin, preferably β-cyclodextrin, at 20° C. to 80° C. or the acids of the compounds of formula (I) as defined above in the Summary in the form of the aqueous solutions of their salts (e.g., sodium or potassium salts) can be admixed with a cyclodextrin and after solution with the equivalent amount of an acid (e.g., HCl or $H_2SO_4$) to afford the corresponding cyclodextrin clathrate.

At this point or after cooling, the corresponding cyclodextrin clathrates separate in the form of crystals. However, it is also possible to convert oily and also crystalline compounds of formula (I), as defined above in the Summary, by rather long stirring (e.g., for 1 hour to 14 days) at ambient temperature, by treatment with an aqueous solution of cyclodextrins, into the corresponding cyclodextrin clathrate form. The clathrates can then be isolated as solid, free-flowing crystals by suctioning off the solvents and drying.

By selection of the suitable amounts of cyclodextrins and water it is possible to obtain the new clathrates in a stoichiometric composition with a reproducible content of effective substance. The clathrates can be used in a dry hygroscopic form or in a water-containing, but less hygroscopic form. A typical molar ratio of cyclodextrin to a compound of formula (I) is 2:1 (cyclodextrin:compound).

The following examples illustrate methods to make compounds of formula (I).

EXAMPLES

Example 1

Preparation of a Compound Wherein Z is i).

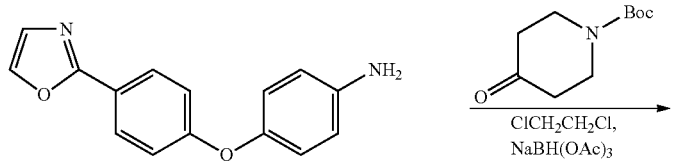

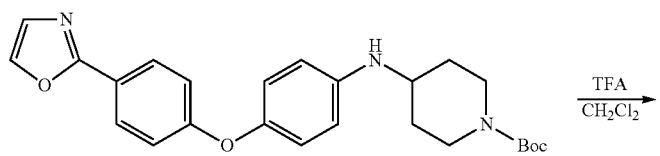

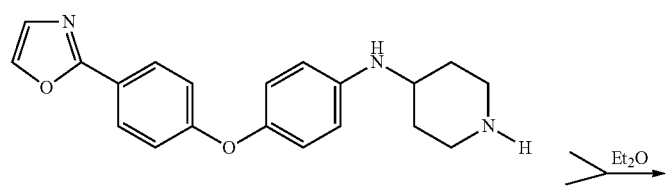

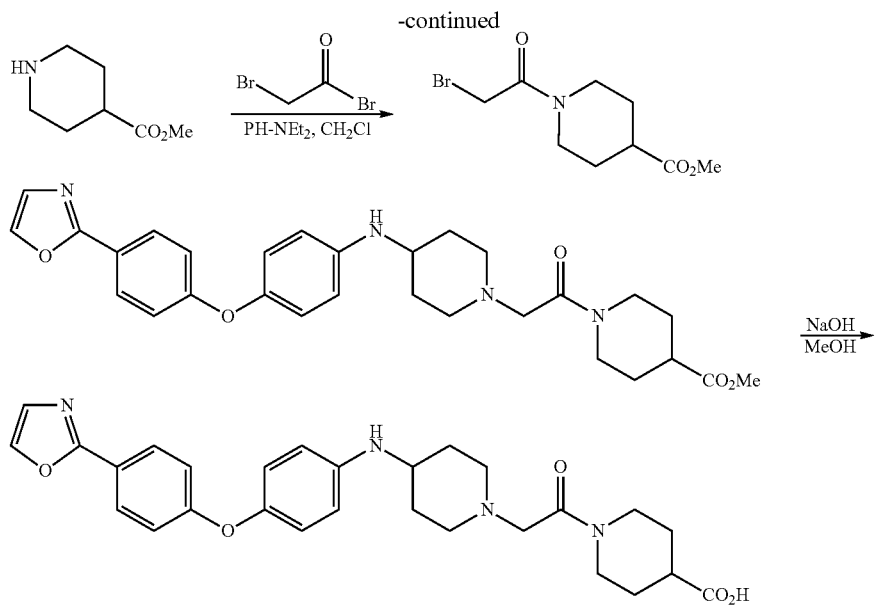

Preparation of 4-((4-(4-(oxazol-2-yl)phenoxy)phenyl)amino)piperidin-1-Boc

To a stirred solution of 4-(4-(oxazol-2-yl)phenoxyaniline (1 eq) and 1-Boc-piperidone (1 eq) in dichloroethane was added triacetoxyborohydride (2 eq). The reaction was stirred until no starting aniline remained. The reaction was diluted with water and extracted with ethyl acetate. The combined organic extracts were washed with brine, dried and concentrated to produce 4-((4-(4-(oxazol-2-yl)phenoxy)phenyl)amino)piperidin-1-Boc.

Preparation of 4-((4-(4-(oxazol-2-yl)phenoxy)phenyl)amino)piperidine

To a stirred solution of 4-((4-(4-(oxazol-2-yl)phenoxy)phenyl)amino)piperidin-1-Boc in dichloromethane was added trifluoroacetic acid. The reaction was stirred until no starting Boc-protected amine remained. The reaction was stirred until no alkyl bromide remained. The reaction was diluted with water, neutralized with aqueous sodium hydroxide and extracted with ethyl acetate. The combined organic extracts were washed with brine, dried and concentrated to produce 4-((4-(4-(oxazol-2-yl)phenoxy)phenyl)amino)piperidine.

Preparation of Methyl N-(2-bromoacetyl)piperidine-4-carboxylate

To a stirred solution of bromoacetyl bromide (1 eq) and diethyl aniline (1.2 eq) in methylene chloride was added a solution of methyl piperidin-4-carboxylate (1 eq) in methylene chloride. The reaction mixture was stirred at ambient temperature until no starting amine remained. The reaction was diluted with water. The organic phase was washed with 1N HCl, water and brine solution, dried over sodium sulfate and concentrated to produce Methyl N-(2-bromoacetyl)piperidine-4-carboxylate.

Preparation of Methyl 1-(2-(4-((4-(4-(oxazol-2-yl)phenoxy)phenyl)amino)piperidin-1-yl)acetyl)piperidine-4-carboxylate To a stirred solution of 4-((4-(4-(oxazol-2-yl)phenoxy)phenyl)amino)piperidine (1 eq) in diethyl ether cooled to 0° C. was added a solution of Methyl N-(2-bromoacetyl)piperidine-4-carboxylate (1 eq) in diethyl ether. The reaction was stirred until no starting alkyl bromide remained. The reaction was diluted with water and extracted with diethyl ether. The combined organic extracts were washed with brine, dried and concentrated to produce Methyl 1-(2-(4-((4-(4-(oxazol-2-yl)phenoxy)phenyl)amino)piperidin-1-yl)acetyl)piperidine-4-carboxylate.

Preparation of 1-(2-(4-((4-(4-(oxazol-2-yl)phenoxy)phenyl)amino)piperidin-1-yl)acetyl)piperidine-4-carboxylic acid To a stirred solution of aqueous sodium hydroxide (1N) in methanol was added Methyl 1-(2-(4-((4-(4-(oxazol-2-yl)phenoxy)phenyl)amino)piperidin-1-yl)acetyl)piperidine-4-carboxylate. The reaction was stirred until no starting ester remained. The reaction was diluted with water, neutralized with aqueous hydrochloric acid (1N) and extracted with ethyl acetate. The combined organic extracts were washed with brine, dried and concentrated to produce 1-(2-(4-((4-(4-(oxazol-2-yl)phenoxy)phenyl)amino)piperidin-1-yl)acetyl)piperidine-4-carboxylic acid.

The compound of Example 1 demonstrated the ability to inhibit: $LTA_4$ hydrolase activity at an $IC_{50}$ value of 2.1 nM; peptidase activity at an $IC_{50}$ value of 7.1 nM; and the production of $LTB_4$ in whole blood at an $IC_{50}$ value of 62 nM.

Example 2

Preparation of a compound wherein Z is ii).

The same reaction sequence as Example 1 is performed wherein

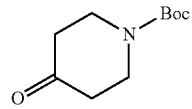 [SMILES: CC(C)(C)OC(=O)N1CCC(=O)CC1]

is replaced with

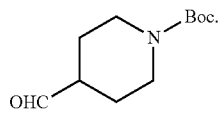 [SMILES: CC(C)(C)OC(=O)N1CCC(C=O)CC1]

Example 3

Preparation of a compound wherein Z is iv).

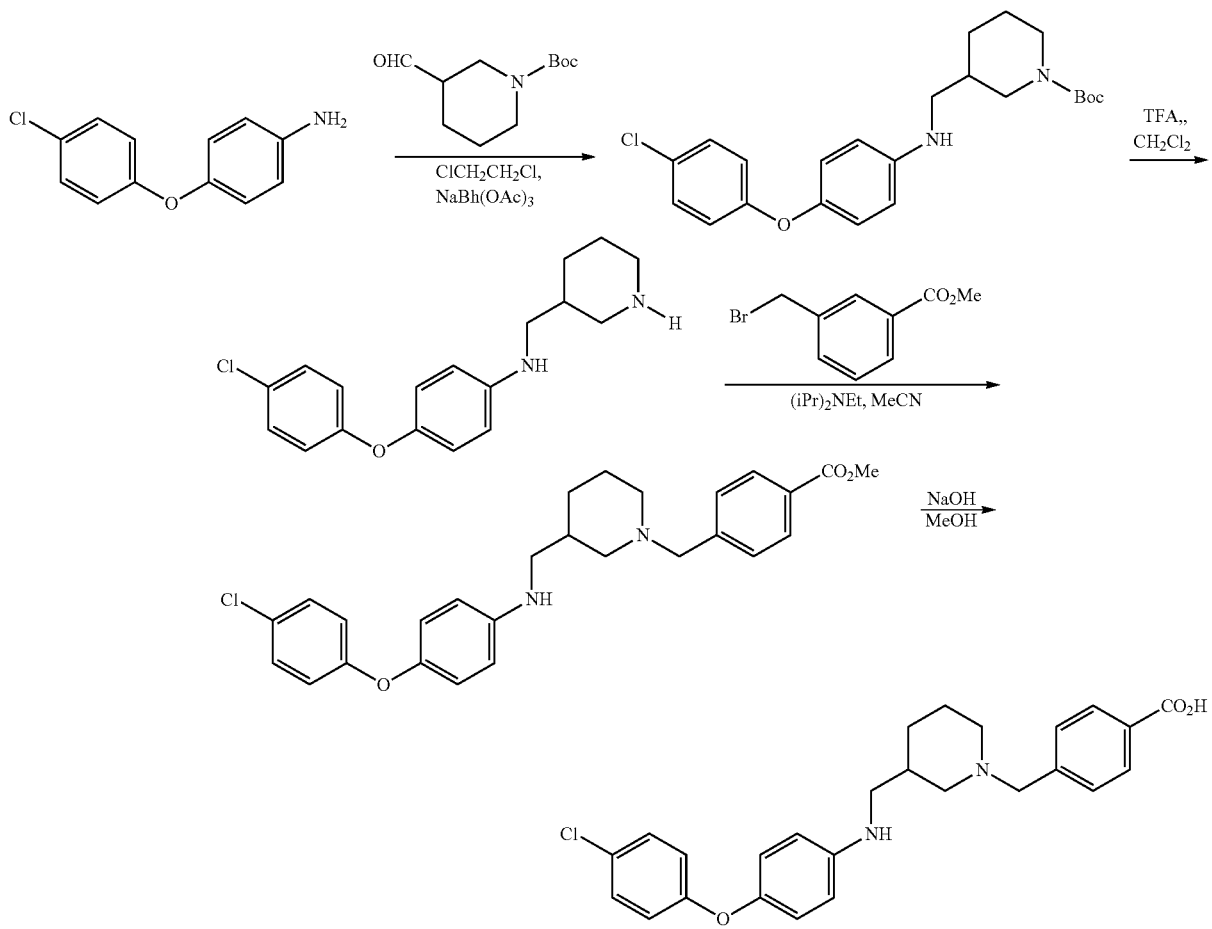

was added trifluoroacetic acid. The reaction was stirred until no starting material remained. The reaction was diluted with water, neutralized with aqueous sodium hydroxide (1N) and extracted with ethyl acetate. The combined organic extracts were washed with brine, dried and concentrated to produce 3-(((4-(4-chlorophenoxy)phenyl)amino)methyl)piperidine.

Preparation of Methyl 4-((3-(((4-(4-chlorophenoxy)phenyl)amino)methyl)piperidin-1-yl)methyl)benzoate To a stirred solution of 3-(((4-(4-chlorophenoxy)phenyl)amino)methyl)piperidine (1 eq) and Hunig's Base (1.1 eq) in Preparation of 3-(((4-(4-chlorophenoxy)phenyl)amino)methyl)-1-Boc-piperidine To a stirred solution of 1-Boc-piperidine-3-carboxaldehyde (1 eq) and 4-chlorophenoxyaniline (1 eq) in 1,2-dichloroethane was added a triacetoxyborohydride (2 eq). The reaction was stirred until no starting aniline remained. The reaction was diluted with water and extracted with ethyl acetate. The combined organic extracts were washed with brine, dried and concentrated to produce 3-(((4-(4-chlorophenoxy)phenyl)amino)methyl)-1-Boc-piperidine.

Preparation of 3-(((4-(4-chlorophenoxy)phenyl)amino)methyl)piperidine

To a stirred solution of 3-(((4-(4-chlorophenoxy)phenyl)amino)methyl)-1-Boc-piperidine (1 eq) in dichloromethane acetonitrile was added a solution of methyl 4-bromomethylbenzoate (1 eq) in acetonitrile. The reaction was stirred until no starting alkyl bromide remained. The reaction was diluted with water and extracted with diethyl ether. The combined organic extracts were washed with brine, dried and concentrated to produce Methyl 4-((3-(((4-(4-chlorophenoxy)phenyl)amino)methyl)piperidin-1-yl)methyl)benzoate.

Preparation of 4-((3-(((4-(4-chlorophenoxy)phenyl)amino)methyl)piperidin-1-yl)methyl)benzoic acid To a stirred solution of hydrochloric acid in methanol was added Methyl 4-((3-(((4-(4-chlorophenoxy)phenyl)amino)methyl)piperidin-1-yl)methyl)benzoate. The reaction was stirred until no starting ester remained. The reaction was diluted with water, neutralized with aqueous hydrochloric acid (1N) and extracted with ethyl acetate. The combined organic extracts were washed with brine, dried and concentrated to produce 4-((3-(((4-(4-chlorophenoxy)phenyl)amino)methyl)piperidin-1-yl)methyl)benzoic acid.

The compound of Example 3 demonstrated the ability to inhibit: LTA$_4$ hydrolase activity at an IC$_{50}$ value of 1.8 nM; peptidase activity at an IC$_{50}$ value of 22 nM; and the production of LTB$_4$ in whole blood at an IC$_{50}$ value of 100 nM.

Example 4

Preparation of a compound wherein Z is iii).
The same reaction sequence as Example 3 is performed wherein

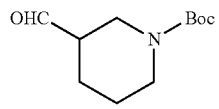

is replaced with

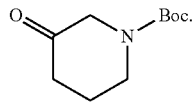

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the following formula (I-A):

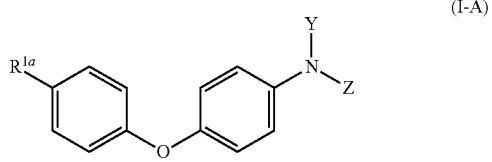

wherein
R$^{1a}$ is hydrogen, halo, haloalkyl, haloalkenyl, haloalkynyl, hydroxyalkyl, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, optionally substituted amidinyl, optionally substituted guanidinyl, —R$^{13}$—OR$^{10}$, —R$^{13}$—C(=O)OR$^{10}$, or —R$^{13}$—C(=O)R$^{10}$;

Y is hydrogen, halo, haloalkyl, haloalkenyl, haloalkynyl, hydroxyalkyl, cyano, optionally substituted alkyl, optionally substituted alkenyl, optionally substituted alkynyl, optionally substituted cycloalkyl, optionally substituted cyoloalkylalkyl, optionally substituted aryl, optionally substituted aralkyl, optionally substituted heteroaryl, optionally substituted heteroarylalkyl, optionally substituted heterocyclyl, or optionally substituted heterocyclylalkyl; and Z is

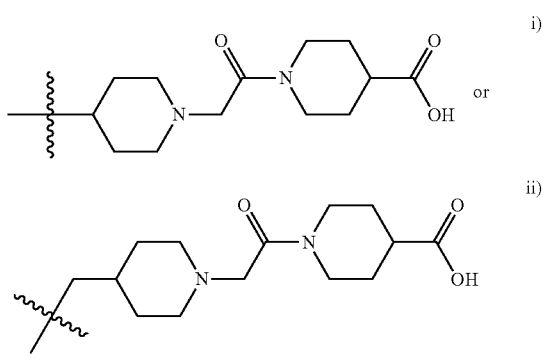

each R$^{10}$ is independently hydrogen, haloalkyl, haloalkenyl, haloalkynyl, hydroxyalkyl, optionally substituted alkyl, optionally substituted alkenyl, optionally substituted alkynyl, optionally substituted aryl, optionally substituted aralkyl, optionally substituted heteroaryl, optionally substituted heteroarylalkyl, optionally substituted heterocyclyl, or optionally substituted heterocyclylalkyl;

each R$^{12}$ is independently an optionally substituted straight or branched alkylene chain, an optionally substituted straight or branched alkenylene chain, or an optionally substituted straight or branched alkynylene chain;

each R$^{13}$ is independently a direct bond, an optionally substituted straight or branched alkylene chain, an optionally substituted straight or branched alkenylene chain, or an optionally substituted straight or branched alkynylene chain;

as a single stereoisomer or as a mixture of stereoisomers;
or a pharmaceutically acceptable salt, ammonium ion, or N-oxide thereof.

2. A compound according to claim 1 wherein R$^{1a}$ is optionally substituted heteroaryl and Z is

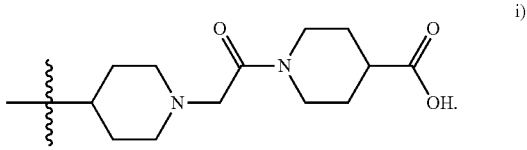 [SMILES: *C1CCN(CC(=O)N2CCC(C(=O)O)CC2)CC1]

3. A compound according to claim 1 wherein the compound is 1-(2-(4-((4-(4-(oxazol-2-yl)phenoxy)phenyl)amino)piperidin-1-yl)acetyl)piperidine-4-carboxylic acid.

4. A compound according to claim 1 selected from a formula in the Table below:

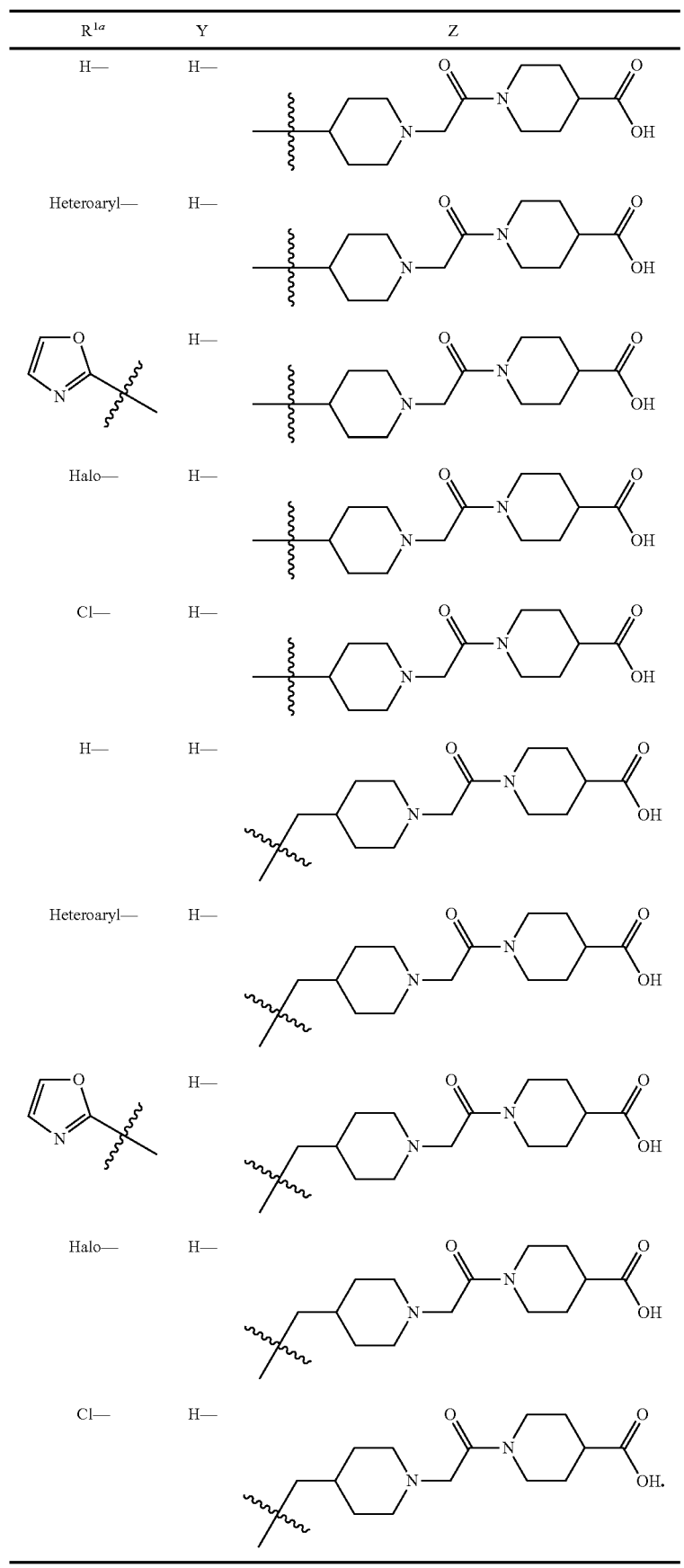

5. A compound according to claim 1 wherein $R^{1a}$ is halo and Z is

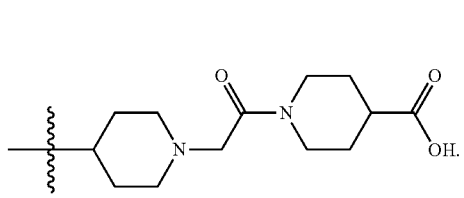
i)

6. A compound according to claim 1 wherein $R^{1a}$ is —Cl and Z is

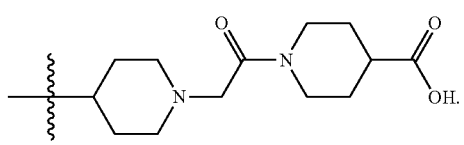
i)

7. A compound of claim 1 wherein $R^{1a}$ is a halo and Z is

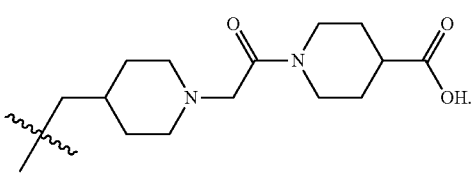
ii)

8. A compound of claim 1 wherein $R^{1a}$ is —Cl and Z is

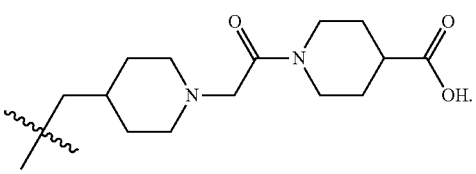 [SMILES: *CC1CCN(CC(=O)N2CCC(C(=O)O)CC2)CC1]
ii)

9. A compound according to claim 1 wherein $R^{1a}$ is optionally substituted heteroaryl and Z is

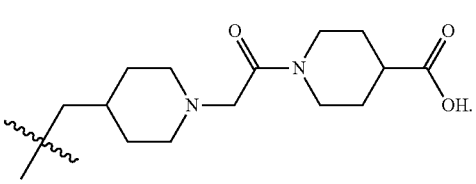
ii)

10. A compound according to claim 1 wherein $R^{1a}$ is

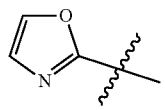

and Z is

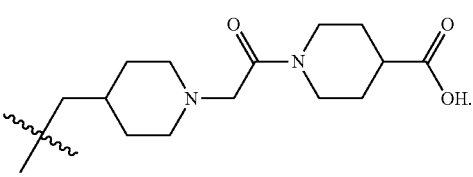
ii)

11. A compound according to claim 1 wherein $R^{1a}$ is

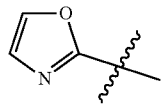

and Z is

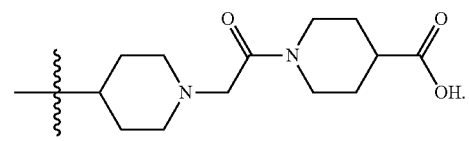
i)

12. A compound according to claim 1 wherein $R^{1a}$ is —H and Z is ii)

13. A compound according to claim 1 wherein $R^{1a}$ is —H and Z is

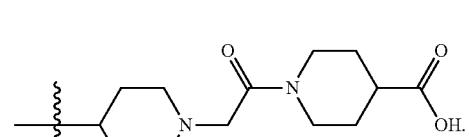
i)

* * * * *